(12) United States Patent
Sun et al.

(10) Patent No.: US 10,054,570 B2
(45) Date of Patent: Aug. 21, 2018

(54) COLORIMETRIC SENSORS FOR ALKYLATING AGENTS

(71) Applicant: THE REGENTS OF THE UNIVERSITY OF CALIFORNIA, Oakland, CA (US)

(72) Inventors: Gang Sun, Davis, CA (US); Sanaz Ghanbari, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 61 days.

(21) Appl. No.: 14/946,597

(22) Filed: Nov. 19, 2015

(65) Prior Publication Data

US 2016/0077070 A1 Mar. 17, 2016

Related U.S. Application Data

(63) Continuation of application No. PCT/US2014/039720, filed on May 28, 2014.

(60) Provisional application No. 61/828,061, filed on May 28, 2013, provisional application No. 61/870,753, filed on Aug. 27, 2013.

(51) Int. Cl.
*G01N 31/22* (2006.01)
*G01N 21/29* (2006.01)
*G01N 21/78* (2006.01)

(52) U.S. Cl.
CPC ........... *G01N 31/22* (2013.01); *G01N 21/293* (2013.01); *G01N 21/78* (2013.01); *G01N 21/783* (2013.01)

(58) Field of Classification Search
CPC ...................................... G01N 31/22
USPC ........................................... 436/101
See application file for complete search history.

(56) References Cited

U.S. PATENT DOCUMENTS

2010/0190658 A1 7/2010 Van der Eycken et al.
2010/0330703 A1 12/2010 Bernstein et al.

OTHER PUBLICATIONS

Eugene Sawicki, D. F. Bender, T. R. Hauser, R. M. Wilson, Jr., and J. E. Meeker "Five New Methods for the Spectrophotometric Determination of Alkylating Agents Including Some Extremely Sensitive Autocatalytic Methods" Analytical Chemistry , vol. 35, No. 10, Sep. 1963 (Year: 1963).*
Kawazoe et al. Chem Pharm Bull. 30(6)2077-2086 1982 (Year: 1982).*
Spears "Nucleophilic Selectivity Ratios of Model and Clinical Alkylating Agents by 4-(4'-Nitrobenzyl)pyridine Competition" Molecular Pharmacology, 19:496-504, 1981 (Year: 1981).*
International Search Report and Written Opinion dated Oct. 1, 2014 in PCT Appln. PCT/US14/39720; 13 pages.

(Continued)

*Primary Examiner* — Christine T Mui
*Assistant Examiner* — Emily R. Berkeley
(74) *Attorney, Agent, or Firm* — Kilpatrick Townsend & Stockton LLP (57) ABSTRACT

Methods and kits for detection of alkylating agents are described. The present invention discloses methods and kits comprising sensors for the rapid detection of chemical agents (e.g., alkylating agents) at low concentrations. The methods are useful for the detection of alkylating agents such as field fumigants such as methyl bromide or methyl iodide. The detection can advantageously be performed by a change in light absorbance of the sensor moiety using the naked eye.

14 Claims, 7 Drawing Sheets

(56) References Cited

OTHER PUBLICATIONS

Gomez-Bombarelli, R. et al.; "Potential of the NBP Method for the Study of Alkylation Mechanisms: NBP as a DNA-Model"; *Chem. Res. Toxicol.*; vol. 25; pp. 1176-1191; 2012.

Hertzog-Ronen, C. et al.; "Detection and Identification of Alkylating Agents by Using a Bioinspired 'Chemical Nose'"; *Chem. Eur. J,*; vol. 15; pp. 10380-10386; 2009.

Ghanbari, S. et al.; "Colorimetric Sensor for Fumigants"; $41^{st}$ Annual Agricultural and Environmental Chemistry Wnter Colloquium Abstracts Book; University of California, Davis; pp. 1-20; Feb. 2013.

\* cited by examiner

Figure 1. Color changes of NBP under varied concentrations. Temp= 100 °C; Methyl iodide=1000 ppm; Reaction time =1 hour. Wavelength= 575 nm. Base = triethylamine

Figure 2 Color changes of NBP solution under different temperatures. NBP=10%; Methyl iodide=1000 ppm; Reaction time =1 hour. Wavelength= 575 nm. Base = triethylamine

Figure 3 Color changes under different reaction time. NBP=10%; Methyl iodide=1000 ppm; Reaction temperature = 100 C. Wavelength= 575 nm. Base = triethylamine

Figure 4. Color changes of NBP solution against concentrations of Mel. NBP = 10%, reaction temperature=100 C, and reaction time =1 hour.

Figure 5. Color changes of NBP solution against concentrations of MeBr. NBP = 10%, reaction temperature=100 C, and reaction time =1 hour.

MeI Strip:
    60 μL of %80 NBP
    2 min exposure
    Microfiber Paper                                   control 10 ppm    5 ppm    1 ppm    800 ppb    600 ppb    400 ppb    200 ppb

Figure 7B

MeBr Strip:
    60 μL of %80 NBP
    3 min exposure
    Microfiber Paper                                   control 20 ppm    10 ppm    5 ppm    1 ppm    800 ppb

COLORIMETRIC SENSORS FOR ALKYLATING AGENTS

CROSS REFERENCE TO RELATED APPLICATIONS

This application is a continuation application of PCT/US2014/039720, filed May 28, 2014, which application claims priority to U.S. Provisional Application No. 61/828,061, filed on May 28, 2013 and U.S. Provisional Application No. 61/870,753 filed on Aug. 27, 2013; which applications are all incorporated herein by reference in their entireties.

BACKGROUND OF THE INVENTION

Detection of chemical agents at diluted concentrations is important for the safety of workers in certain areas such as farm workers in the field, soldiers in the field, hospital workers, chemists in production plants and the like.

One illustrative class of potentially harmful chemical agents is fumigants. Fumigants are pesticides in the form of gas that are heavier than air and have the ability to spread to all areas and surfaces. Highly volatile, fumigants are used to sterilize soil before planting crops such as potatoes, carrots and strawberries. Fumigant exposure can cause a variety of adverse health effects, ranging from simple irritation of the skin and eyes to more severe effects such as affecting the nervous system, mimicking hormones causing reproductive problems, and also causing cancer. Communities and farm workers near agricultural fields face serious risks of poisoning from drifting fumigants. The World Health Organization and the UN Environment Program estimate that each year, 3 million workers in agriculture in the developing world experience severe poisoning from pesticides, about 18,000 of whom die. Since fumigants are both toxic and gaseous, their offsite movement can pose hazardous impacts to people in nearby areas. Current quantitative measurement of the fumigants will take days and are quite costly. Thus, rapid, onsite, economic, and accurate detection and indication of exposure and concentrations of fumigants is necessary for human safety and protection of workers.

BRIEF SUMMARY OF THE INVENTION

Any useful tool for detection of chemical agents should provide a rapid, sensitive and visible response to chemical agents. Further, such a detection tool should be easy to manufacture and easy to use for a worker who can be potentially exposed to chemical agents (e.g., alkylating agents). The detection of alkylating agents such as fumigants is not trivial because they are highly reactive and have low molecular weights. The present invention aims for the development of sensors for rapid detection of chemical agents (e.g., alkylating agents) at low concentrations.

This invention provides methods and kits for rapid detection of alkylating agents (e.g., fumigants, agents of chemical warfare, and the like) and development of sensors that can rapidly identify and quantify chemical agents (e.g., fumigants, agents of chemical warfare, alkylating agents, and the like). In specific instances, the alkylating agents are gas phase alkylating agents. The methods and kits provided herein detect alkylating agents in low concentrations (e.g., ppm or ppb concentrations). In some cases, advantageously, the methods and kits provided herein do not require the use of additional chemicals (e.g., alkali) nor elevated temperatures for detection of alkylating agents in low concentrations (e.g., ppm or ppb concentrations). The methods and kits provided herein are easy to manufacture and easy to use. In some embodiments, the methods and kits provided herein are wearable, i.e., they are compact and can be easily attached to a worker's clothing, or worn as a badge, or a wrist band, or the like.

Described herein is a method for detecting alkylating agents, the method comprising, consisting essentially of, or consisting of: contacting the alkylating agent with a sensor moiety of the formula:

Formula I wherein R, when present, is selected from thiophenyl, or a pi-conjugated oligomer, where the wavy line indicates the point of attachment to the rest of the molecule; and detecting a change in light absorbance of the sensor moiety. The subscripts 0-1; 1-2; and 0-2; mean 0 or 1; 1 or 2; or 0, or 1, or 2, respectively.

In certain aspects, the sensor moiety can optionally comprise an additive such as a reducing agent. Suitable reducing agents include, but are not limited to, sodium hydrosulfite ($Na_2S_2O_4$) or sodium thiosulfate ($Na_2S_2O_3$).

Also described herein is a kit for detection of alkylating agents, the kit comprising, consisting essentially of, or consisting of:
(i) a solid support;
(ii) a container comprising a solution of a sensor moiety, optionally with an additive in a solvent, wherein the sensor moiety has the formula Formula I wherein R, when present, is selected from thiophenyl, or a pi-conjugated oligomer, where the wavy line indicates the point of attachment to the rest of the molecule; and (iii) an optional color chart for quantification of the alkylating agent.

In certain aspects, the solution of the sensor moiety can also comprise an additive such as a reducing agent. Suitable reducing agents include sodium hydrosulfite ($Na_2S_2O_4$) or sodium thiosulfate ($Na_2S_2O_3$).

These and other aspects, object and embodiments will become more apparent when read with the following figures and detailed description which follows.

BRIEF DESCRIPTION OF THE DRAWINGS

FIGS. 1A-B show a picture of the color changes and UV-vis absorbance at 575 nm. The impact of NBP concentration on the color change was evaluated (FIG. 1B). The concentration of NBP was varied from 0.1%, 0.5%, 1%, 5% and 10%, and the color intensity increased with increasing concentration of NBP (FIG. 1A). A test concentration of NBP at 10% was employed in the following tests described in FIGS. 2-5 and Examples 1-5.

(FIG. 3A). The reaction time was changed from 1 min, to 5 min, 15 min, 30 min, 45 min, and 60 min, respectively. Longer reaction time resulted in darker color in solutions. 15 minutes or longer reaction time provided visually detectable (to naked human eye) dark blue color in the solution (FIG. 3B).

FIGS. 7A-B show the results from the experiment described in Example 8. NBP was dissolved in acetophenone to reach 80% wt concentration. A filter paper strip was saturated with a certain amount of the solution. The paper based sensor was exposed to vaporous gases in a gas chamber for less than two minutes. A blue color appeared and was compared with a color chart quantifying the amount of the chemical in the vapor. FIG. 7A shows results following exposure to methyl iodide. FIG. 7B shows results following exposure to methyl bromide.

DETAILED DESCRIPTION OF THE INVENTION

Provided herein are methods for detection of chemical agents in the presence of a sensor moiety of Formula I or Formula II. The methods of detection described herein are capable of detecting chemical agents (e.g., alkylating agents) at low concentrations, are easy to use, and are inexpensive. In one embodiment, provided herein are solid-support-based (e.g., paper-based) colorimetric sensors for detection of alkylating agents (e.g., fumigants).

Definitions

As used herein, a "sensor moiety" is a moiety which undergoes a chemical or physical change (e.g., one or more of electron transfer, proton abstraction, protonation, covalent bond formation, electrostatic bond formation or any other such transformation) when contacted with an agent of interest. The chemical or physical change consequently causes a change in absorbance of light. In some cases, the change in visible light absorbance is associated with a colorimetric change which is detectable visually (e.g., by naked eye, by UV-Vis spectrometer, or any other suitable technique). The sensor moiety may be contacted with any chemical agent including, but not limited to, an alkylating agent, a fumigant, a chemical warfare agent, etc.

As used herein a "pi-conjugated oligomer" is a moiety having extended chains of alternating single and double bonds. For example, a pi-conjugated oligomer comprises aromatic or heteroaromatic units that are linked together by single bonds. Aromatic or heteroaromatic units include for example, benzene, thiophene, benzothiophene and the like. Depending on the length of the chains, i.e., the number of repeating monomer units present in the pi-conjugated moiety, the moiety may be a pi-conjugated oligomer or polymer. The presence of pi-conjugated oligomers in the sensor moieties of formula I, in some cases, enhances the ability to detect alkylating agents. Some non-limiting examples of pi-conjugated oligomers are:

thiophenyl,

As used herein, "alkaline conditions" means in the presence of a base. Bases which are suitable for the induction of alkaline conditions may be organic bases or inorganic bases. Examples of organic bases include, but are not limited to, triethylamine, diisopropyl amine, diisopropylethylamine, aniline, pyrrolidine, morpholine, pyridine or piperazine. Examples of inorganic bases include, but are not limited to, potassium hydroxide, sodium hydroxide, lithium hydroxide, barium hydroxide, magnesium hydroxide, sodium carbonate, potassium carbonate, sodium bicarbonate, or potassium bicarbonate.

As used herein, "detecting" or "detection" is associated with an observation of a change in absorbance. The change in absorbance may be colorimetric and may be visible to the naked human eye, or the change in absorbance is measurable by a machine (e.g., a UV-vis spectrometer).

As used herein, a "reducing agent" includes a compound that loses (or "donates") an electron to another chemical species in a redox chemical reaction. Since the reducing agent is losing electrons, it is said to have been oxidized. A reducing agent typically is in one of its lower possible oxidation states and is known as the electron donor. Examples of reducing agents include the earth metals, formic acid, and sulfite compounds.

Methods

Provided herein are methods for detecting an alkylating agent, the method comprising: contacting the alkylating agent with a sensor moiety of Formula I as described in the summary and the claims. In some embodiments, provided herein is a method for detecting alkylating agents, the method comprising, consisting essentially of, or consisting of: contacting the alkylating agent with a sensor moiety of the formula:

Formula IA wherein R, when present, is selected from or a pi-conjugated oligomer, where the wavy line indicates the point of attachment to the rest of the molecule; and detecting a change in light absorbance of the sensor moiety. The change in the sensor moiety can be physical or chemical.

In certain aspects, the sensor moiety can optionally comprise an additive such as a reducing agent. Suitable reducing agents include, but are not limited to, sodium hydrosulfite ($Na_2S_2O_4$) or sodium thiosulfate ($Na_2S_2O_3$).

In certain embodiments of compounds of Formula I or Formula IA, R, when present, is selected from —$CH_2$-phenyl-p-$NO_2$, thiophenyl, —$CH_2$-naphthyl-p-$NO_2$, or a pi-conjugated oligomer. In some embodiments of compounds of Formula I or Formula IA, R, when present, is selected from —$CH_2$-phenyl-p-$NO_2$, thiophenyl, or —$CH_2$-naphthyl-p-$NO_2$. In some embodiments of compounds of Formula I or Formula IA, R, when present, is selected from —$CH_2$-phenyl-p-$NO_2$, —$CH_2$-phenyl-m-$NO_2$, —$CH_2$-phenyl-o-$NO_2$, thiophenyl, —$CH_2$-naphthyl-p-$NO_2$, —$CH_2$-naphthyl-m-$NO_2$, —$CH_2$-naphthyl-o-$NO_2$, or a pi-conjugated oligomer. As used herein, the designations p, m, o refer to para, meta or ortho substituents. For example, —$CH_2$-naphthyl-p-$NO_2$ refers to a para-nitro group where the nitro group is para with respect to the point of attachment to the pyridine ring: i.e., a sensor moiety comprising —$CH_2$-naphthyl-p-$NO_2$ is or and or the like. For example, —CH$_2$-naphthyl-m-NO$_2$ refers to a meta-nitro group where the nitro group is meta with respect to the point of attachment to the pyridine ring: i.e., a sensor moiety comprising —CH$_2$-naphthyl-m-NO$_2$ is or the like.

In some embodiments of the methods, the sensor moiety is selected from the group consisting of In a specific instance, the sensor moiety is 4-(p-nitrobenzyl)-pyridine (NBP) having the structure:

In another specific instance, the sensor moiety is 4-(thiophen-3-yl)pyridine having the structure:

wherein the subscript is (NO$_2$)$_0$.

In one group of embodiments, the alkylating agent is a fumigant. In one group of embodiments, the fumigant is a field fumigant. In some embodiments, the field fumigant is selected from the group of methyl bromide, methyl iodide, formaldehyde, 1,3 dichloropropene, ethylene dibromide and methyl isothiocyanate. In other embodiments, the field fumigant is selected from the group consisting of methyl bromide, methyl iodide, 1,3 dichloropropene, formaldehyde and ethylene dibromide. In further embodiments, the field fumigant is selected from the group consisting of methyl bromide, 1,3 dichloropropene, and methyl iodide.

In some embodiments, the detection is carried out visually by contacting the alkylating agent (e.g., a fumigant) with a solution comprising the sensor moiety. The contact between the alkylating agent and the sensor moiety and the subsequent colorimetric change may occur under various conditions, singly, or under combinations of conditions as described below.

In some embodiments, there are interferences with sensing. For example, chloropicrin can interfere with the sensor detection of methyl bromide. In certain aspects, a reducing agent such as sodium hydrosulfite can remove the interference. Chloropicrin is an oxidative compound which can be reduced by this agent.

In some cases, for the methods described above, the detection is carried out visually (e.g., with a naked human eye). In some other cases, for the methods described above, the detection is carried out with a UV-Vis spectrometer. In one group of embodiments, a colorimetric change is detected. In some cases the colorimetric change occurs under ambient conditions. In some other cases the colorimetric change occurs under alkaline conditions (e.g., the solution comprising a sensor moiety of formula I is alkaline). In some cases, the colorimetric change is detected by contacting the alkylating agent with the sensor moiety in the absence of a base, then a base is added in a separate step and a color change is detected under alkaline conditions. In some embodiments, the detectable colorimetric change occurs at elevated temperature. In some cases, the detectable colorimetric change occurs when both alkaline conditions and elevated temperature are present.

In some instances, the detection is carried out visually by contacting the fumigant with a solution comprising the sensor moiety without the use of alkaline conditions and/or heat. In some of such embodiments, the solvent for the solution comprising the sensor moiety is a ketone. In some specific embodiments, the solvent for the solution comprising the sensor moiety is acetophenone. Advantageously, when acetophenone is a solvent, the detectable colorimetric change, subsequent to contacting the fumigant with a solution of the sensor moiety of formula I, is observed under ambient conditions (e.g., without the use of alkaline conditions and/or heat).

In another group of embodiments, the detection is carried out visually by contacting the fumigant with a solution comprising the sensor moiety under alkaline conditions and detecting a color change under alkaline conditions. In yet other embodiments, the detection is carried out visually by contacting the fumigant with a solution comprising the sensor moiety at an elevated temperature and detecting a color change at the elevated temperature. In further embodiments, the detection is carried out visually by contacting the fumigant with a solution comprising the sensor moiety under alkaline conditions and at elevated temperature and detecting a color change under alkaline conditions and at elevated temperature. In some of such embodiments, the solvent for the solution comprising the sensor moiety is an alcohol. In some specific embodiments, the solvent for the solution comprising the sensor moiety is ethylene glycol. In some cases, when ethylene glycol is a solvent, the detectable colorimetric change, subsequent to contacting the fumigant with a solution of the sensor moiety of formula I, is observed under alkaline conditions (i.e., in the presence of a base). In some cases, when ethylene glycol is a solvent, the detectable colorimetric change, subsequent to contacting the fumigant with a solution of the sensor moiety of formula I, is observed at elevated temperature (e.g., by autoclaving the test sample). In some cases, when ethylene glycol is a solvent, the detectable colorimetric change, subsequent to contacting the fumigant with a solution of the sensor moiety of formula I, is observed under alkaline conditions (i.e., in the presence of a base) and at elevated temperature (e.g., by autoclaving the test sample).

Also contemplated within the scope of embodiments presented here are various solvents for dissolution of the sensor moiety, including organic solvents, water, or mixtures of solvents. In one group of embodiments, the solvent is a ketone, e.g., acetone, methyl ethyl ketone, methyl isobutyl ketone, or other suitable solvents. In another group of embodiments, the solvent is an alcohol (e.g., ethanol, butanol, ethylene glycol) or an ether (e.g., tetrahydrofuran). Optionally the solvent chosen is water miscible. In some cases, the sensor moiety is dissolved in a solvent and the solution is made alkaline prior to contact with the alkylating agent.

In one embodiment, the alkylating agent (e.g., a fumigant), which is contacted with a sensor moiety of Formula I, is in gaseous form. In another embodiment, the alkylating agent (e.g., a fumigant), which is contacted with a sensor moiety of Formula I, is in liquid form.

In one embodiment of the present methods, the solution of the sensor moiety of Formula I is placed on a solid support, e.g., a filter paper base, a microfiber membrane, or a nanofiber membrane. Contemplated within the scope of the methods is the use of testing strips, beads, films, or patches for detection of alkylating agents (e.g., fumigants). In one non-limiting illustrative example, filter paper strips are soaked (e.g., saturated) with a solution of the sensor moiety of Formula I. The filter paper strips with the sensor moiety of Formula I adsorbed on the filter paper strips are incorporated in kits or used directly for detection of alkylating agents. The solution of the sensor moiety of Formula I may comprise a base, or the filter paper strip is exposed to a base after contact with the alkylating agent. Alternatively, the filter paper strip is autoclaved after contact with the alkylating agent.

In accord with the methods described herein, the following reaction equation between a sensor moiety of formula I and alkylating agents demonstrates the mechanism of contacting an alkylating agent R'-LG with a sensor moiety:

R'=alkyl; LG=leaving group.

For instance, the following reaction equation between NBP and methylating agents shows a mechanism of color changes:

-continued

Blue colored

R=Methyl; X=I, or Br.

It was found that when a solution of a sensor moiety of formula I is placed on a solid support and then exposed to an alkylating agent, a colorimetric change is observed even in the absence of additional chemicals (e.g., alkali) and/or elevated temperatures. It was found that when a solution of a sensor moiety is prepared in acetophenone and then exposed to an alkylating agent, a colorimetric change is observed even in the absence of additional chemicals (e.g., alkalis) and/or elevated temperatures.

Table 1 below shows certain assay data for methyl iodide and methyl bromide. FIGS. 4A-B and 5A-B describe the test conditions.

TABLE 1

| Summary of detection limits of MeI and MeBr at UV-vis = 575 nm (blue color) | | | | | | | | | |
|---|---|---|---|---|---|---|---|---|---|
| Concentration (ppm) | 1 | 5 | 10 | 50 | 100 | 200 | 300 | 400 | 500 |
| UV-vis absorbance MeI | 0.2 | 0.21 | 0.21 | 0.3 | 0.4 | 0.6 | 1.0 | 1.3 | 1.9 |
| MeBr | 0.2 | 0.2 | 0.2 | 0.24 | 0.32 | 0.42 | / | / | / |

Kits

Provided herein are kits for detection of alkylating agents, the kits comprising
(i) a solid support;
(ii) a container comprising a solution of a sensor moiety, optionally an additive in a solvent, wherein the sensor moiety has the formula Formula I wherein R, when present, is selected from thiophenyl, or a pi-conjugated oligomer, where the wavy line indicates the point of attachment to the rest of the molecule; and
(iii) an optional color chart for quantification of the alkylating agent.

The kits further comprise instructions for using the kits. An optional color chart is enclosed within a package, which provides a correlation between color and/or color intensity and the amount of alkylating agent. The instructions include the steps of dipping the solid support in the solution comprising the sensor moiety of formula I and exposing the solid support to an alkylating agent or an area suspected of having an alkylating agent.

In certain aspects, the solution of the sensor moiety can comprise an additive such as a reducing agent. Suitable agents include, but are not limited to, sodium hydrosulfite ($Na_2S_2O_4$) or sodium thiosulfate ($Na_2S_2O_3$).

Also contemplated within the scope of embodiments described herein is a kit for detection of alkylating agents, the kit comprising a solid support pre-saturated with a solution of a sensor moiety in a solvent, wherein the sensor moiety has the formula

Formula I wherein R, when present, is selected from thiophenyl, or a pi-conjugated oligomer, where the wavy line indicates the point of attachment to the rest of the molecule. Optionally such a kit has a window for exposure to an alkylating agent and the kit is wearable (e.g., as a badge, a wrist band or the like).

In some embodiments, the kits comprise a sensor moiety selected from the group consisting of and In a specific instance, the sensor moiety is 4-(p-nitrobenzyl)-pyridine (NBP). In another specific instance, the sensor moiety is 4-(thiophen-3-yl)pyridine.

In one group of embodiments, the kit is used for detection of a field fumigant. In some embodiments, the field fumigant is selected from the group consisting of methyl bromide, methyl iodide, formaldehyde, 1,3 dichloropropene, ethylene dibromide and methyl isothiocyanate. In other embodiments, the field fumigant is selected from the group consisting of methyl bromide, methyl iodide, 1,3 dichloropropene, formaldehyde and ethylene dibromide. In further embodiments, the field fumigant is selected from the group consisting of methyl bromide, 1,3 dichloropropene, and methyl iodide.

In one group of embodiments, the kits comprise a solvent selected from a ketone or an alcohol. In some cases, a kit further comprises an alkaline base. In some cases, a kit further comprises a means for heating the solid support.

In one group of embodiments, the sensor moiety in the kit is 4-(p-nitrobenzyl)-pyridine (NBP), and the solvent in the container is acetophenone. In such embodiments, the detection of the alkylating agent is carried out visually by contacting the alkylating agent with a solution comprising the sensor moiety without the use of alkaline conditions and/or heat.

In a different group of embodiments, the kits comprise the sensor moiety 4-(p-nitrobenzyl)-pyridine (NBP), and the solvent is ethylene glycol. In such embodiments, the kit comprises an alkaline base and the detection is carried out visually by detecting a color change under alkaline conditions. In alternative embodiments, the kit comprises the sensor moiety 4-(p-nitrobenzyl)-pyridine (NBP) and the solvent ethylene glycol; the kit further comprises a means for heating the solid support; and the detection is carried out visually at elevated temperature. In additional embodiments, the kit comprises the sensor moiety 4-(p-nitrobenzyl)-pyridine (NBP) and the solvent ethylene glycol; the kit further comprises an alkaline base and a means for heating the solid support; and the detection is carried out visually under alkaline conditions and at elevated temperature.

In one group of embodiments, the kit for detection of an alkylating agent is used for detection of a fumigant. In one group of embodiments, the kit is a badge with a window for exposure to an alkylating agent. In some cases the solid support in the kit is in the form of strips, patches, beads or fibers. In some cases, the solid support in the kit comprises filter paper strips, microfiber membranes or nanofiber membranes.

In one group of embodiments, the alkylating agent which is contacted with a sensor moiety of Formula I in the kit, is in gaseous form. In another group of embodiments, the alkylating agent which is contacted with a sensor moiety of Formula I in the kit, is in liquid form.

In a group of embodiments, for any of the methods and kits described above, the sensor moiety solution comprises the sensor moiety of Formula I in a solvent (e.g., acetophenone or ethylene glycol) in a concentration of about 10-100% by weight of the solution. In a group of embodiments, for any of the methods and kits described above, the sensor moiety solution comprises the sensor moiety of Formula I in a solvent (e.g., acetophenone or ethylene glycol) in a concentration of about 40-100%, such as 40%-80% by weight of the solution. In a group of embodiments, for any of the methods and kits described above, the sensor moiety solution comprises the sensor moiety of Formula I in a solvent (e.g., acetophenone or ethylene glycol) in a concentration of about 10-80% such as 60-80% by weight of the solution. In a group of embodiments, for any of the methods and kits described above, the sensor moiety solution comprises the sensor moiety of Formula I in a solvent (e.g., acetophenone or ethylene glycol) in a concentration of about 40-80% such as 60-80% by weight of the solution. In a group of embodiments, for any of the methods and kits described above, the sensor moiety solution comprises the sensor moiety of Formula I in a solvent (e.g., acetophenone or ethylene glycol) in a concentration of about 60-80% by weight of the solution. In a group of embodiments for the methods and kits described above, the sensor moiety solution comprises the sensor moiety of Formula I in a solvent (e.g., acetophenone or ethylene glycol) in a concentration of about 10-50% or such as 60-80% by weight of the solution.

In a group of embodiments for the methods and kits described above, the sensor moiety solution comprises the sensor moiety of Formula I in a solvent (e.g., acetophenone or ethylene glycol) in a concentration of about 10-100% such as 10-35% or such as 60-80% such as 60, 61, 62, 63, 64, 65, 66, 67, 68, 69, 70, 71, 72, 73, 74, 75, 76, 77, 78, 79, or 80% w/w of the solution. In a group of embodiments for the methods and kits described above, the sensor moiety solution comprises the sensor moiety of Formula I in a solvent (e.g., acetophenone or ethylene glycol) in a concentration of about 10-100% or 20-35% or such as 60-80% by weight of the solution.

In certain instances, a very concentrated amount of sensor moiety is used (e.g., NBP) in acetophenone (80% w/w or a saturated solution). Without being bound by any particular theory, it is believed that sensor moiety is acting as a base and the excess amount of it will drive the reaction to completion with optional heating.

In some embodiments, the methods and/or kits described above allow for detection of the alkylating agent up to a concentration of about 1-5 ppm. In some embodiments, the methods and/or kits described above allow for detection of the alkylating agent up to a concentration of about 0-2 ppm. In some embodiments, the methods and/or kits described above allow for detection of the alkylating agent up to a concentration of about 1-200 ppb. In some embodiments, the methods and/or kits described above allow for detection of the alkylating agent up to a concentration of about 1-800 ppb.

Optionally, the sensitivity of the methods and kits described above is enhanced by addition of an amplification moiety to the solution and/or by attaching an amplification moiety to a sensor of Formula I. As used herein, an "amplification moiety" is a moiety that increases the intensity of color developed after contacting a chemical agent with a sensor moiety of Formula I. In some embodiments, the amplification moiety is covalently attached to the sensor moiety of Formula I (e.g., a chromophore such as retinal, or an anthocyanin, is attached to the sensor moiety, or a fluorophore such as derivatives of fluorescein or rhodamine is attached to the sensor moiety). In other embodiments, the amplification moiety is added to the solution of the sensor of Formula I.

Further contemplated within the scope of embodiments presented herein is a sensor moiety of the formula:

Formula II wherein R, when present, is selected from thiophenyl, or a pi-conjugated oligomer, where the wavy line indicates the point of attachment to the rest of the molecule; and n is 2 or more such as 2, 3, 4, 5, 6, 7, or 8. In some instances, n is 2 to 5. In some of such embodiments, dimerization of sensor moieties of Formula I provides sensor moieties of formula II. In some instances, the use of sensor moieties of formula II in the methods and kits described herein enhances the intensity of color developed after contacting a chemical agent with a sensor moiety. Non-limiting examples of sensor moities of formula II include:

and

In one group of embodiments for the methods and kits described above, the detection is carried out at ambient temperature. In another group of embodiments for the kits described above, the detection is carried out at elevated temperature.

In some specific embodiments, the methods and kits described above provide single use colorimetric sensors for gaseous Methyl Iodide and Methyl Bromide fumigants where the sensors comprise acetophenone solutions of NBP and do not require the use of alkalis or elevated temperatures to obtain a colorimetric change. Provided herein are paper based colorimetric sensors that can rapidly detect very low concentrations of methyl iodide and methyl bromide in air which are suitable for use in the methods and kits described herein. When the methods and kits described above are employed, the detection limit for methyl iodide is about 200 ppb and for methyl bromide is about 800 ppb. The sensor moieties and methods and kits described above are suitable for use in agricultural fields and other aerosol applications in detecting exposure levels of chemicals to humans.

Further provided herein is a system for rapid detection of low concentrations of alkylating agents (e.g., fumigants), the system comprising:
1) providing a colorimetric alkylating agent sensor (e.g., a kit described above) to a subject (e.g., a worker using and/or exposed to fumigants);
2) contacting the alkylating agent sensor with an alkylating agent (e.g., a gaseous or aerosol fumigant);

3) detecting the colorimetric change in the alkylating agent sensor (e.g., a change in a test paper strip).

EXAMPLES

The following examples are offered to illustrate, but not to limit, the claimed invention.

Examples 1-5

Testing Solutions of NBP in Acetophenone

Colorimetric tests for detecting two fumigants, methyl iodide and methyl bromide, using NBP as a sensor moiety and using a solution of NBP in acetophenone are described in FIGS. 1-5. Triethylamine was employed as a base for the experiments.

Example 6

Testing Solutions of NBP in Acetophenone and Ethylene Glycol

Figure 1A:
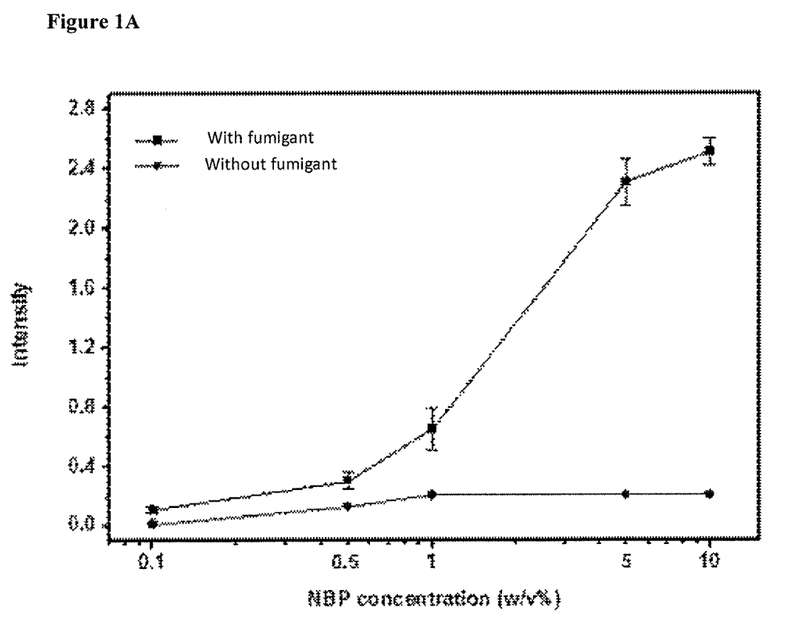
Figure 1B:
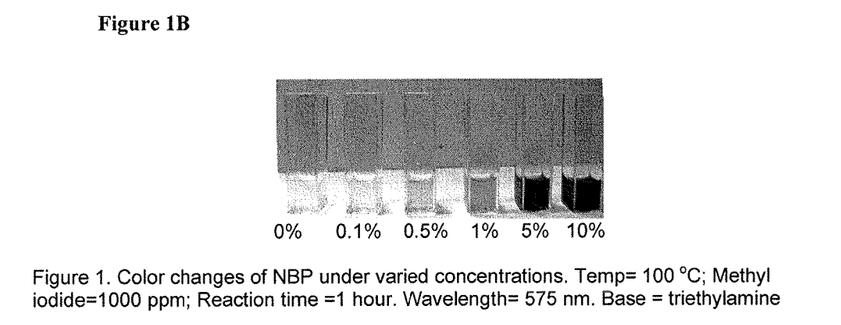
Figure 2A:
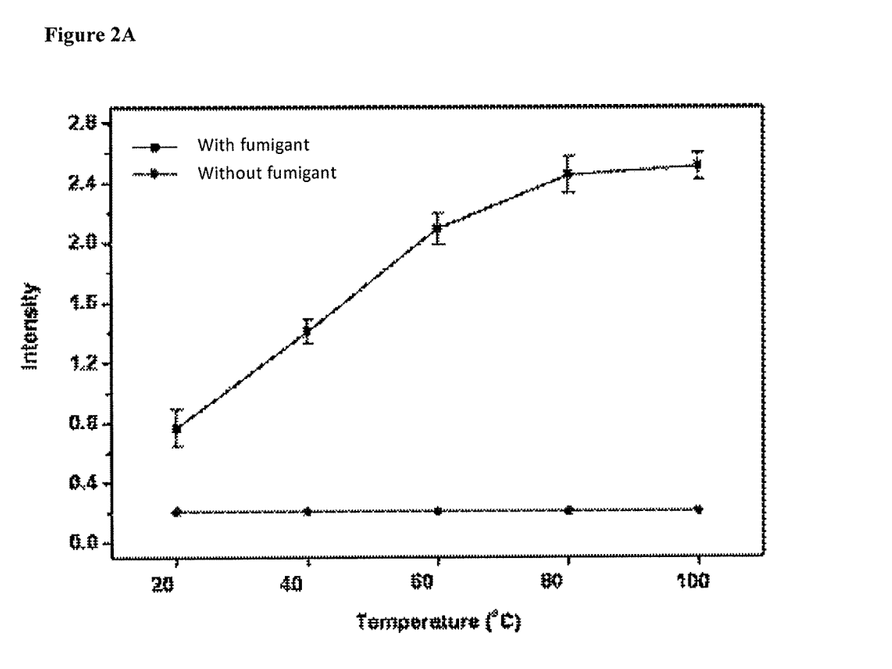
FIGS. 2A-B show the results of color changes under different reaction temperatures, ranging from 20° C. to 100° C. when NBP was used at 10% concentration by weight of the solution and reaction time was 1 hour (FIG. 2A). An elevated reaction temperature resulted in darker color (FIG. 2B).
Figure 2B:
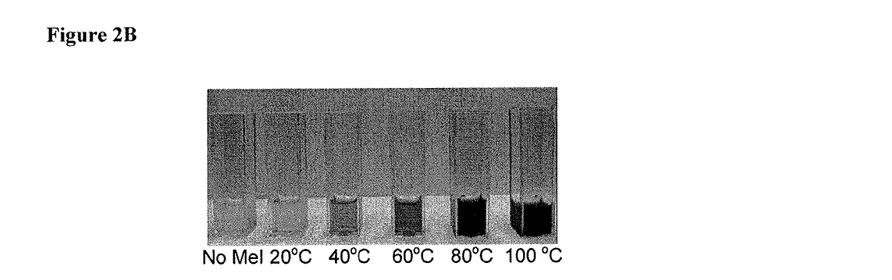
Figure 3A:
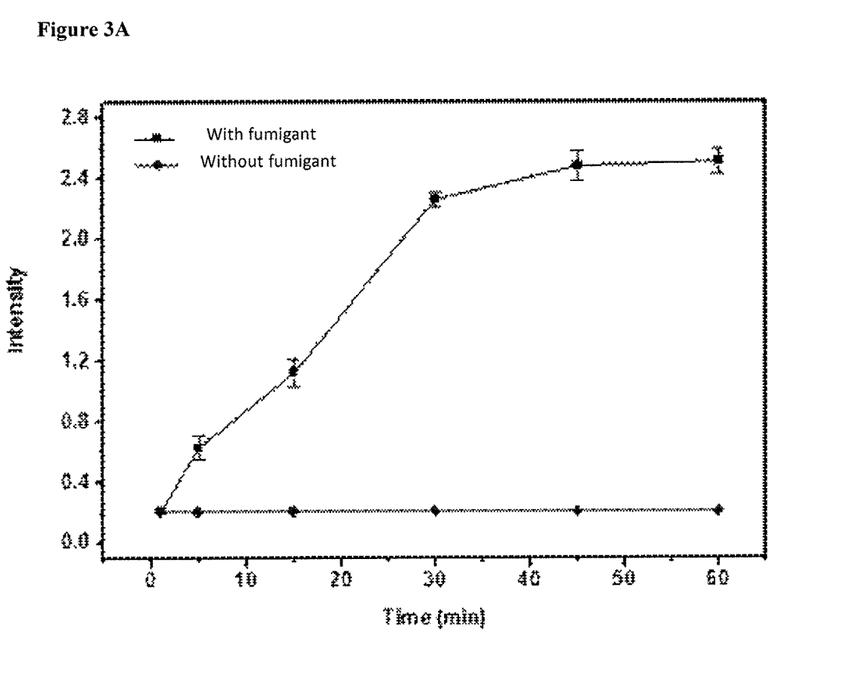
FIGS. 3A-B show the color changes of NBP solutions under different reaction times when NBP concentration was 10% and reaction temperature was 100° C.
Figure 3B:
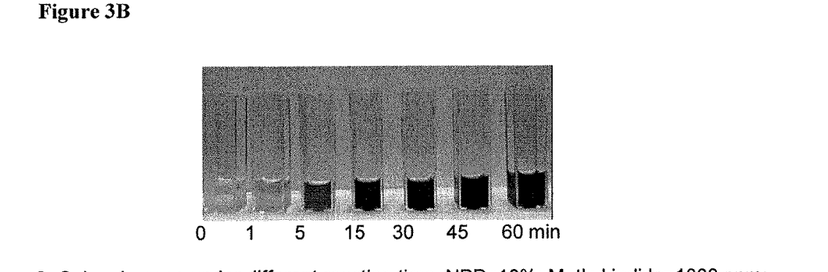
Figure 4A:
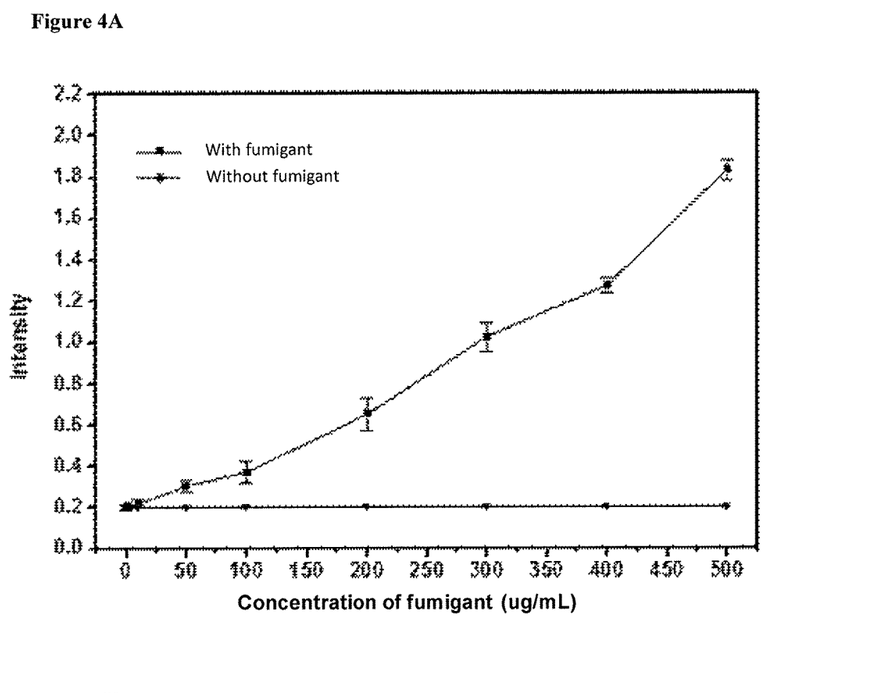
FIGS. 4A-B show color changes of NBP solutions in detecting MeI in different concentrations under following conditions: NBP=10%, reaction temperature=100° C., and reaction time=1 hour (FIG. 4A). The color changes indicated that concentrations of MeI from 5-100 ppm could be detected by comparing the color intensities (FIG. 4B).
Figure 4B:
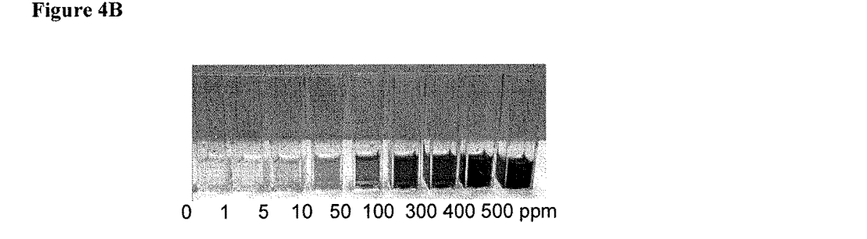
Figure 5A:
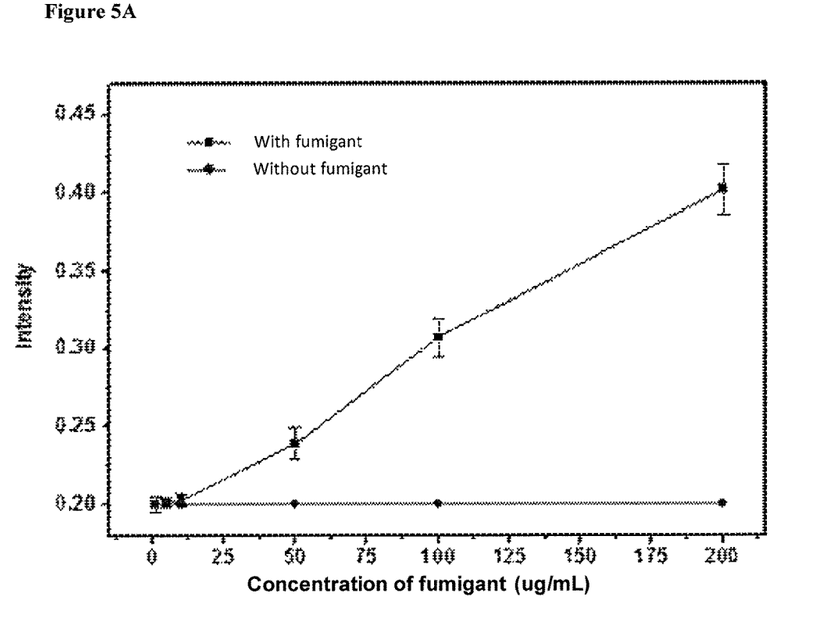
FIGS. 5A-B show color changes of NBP solutions in detecting MeBr in different concentrations under following conditions: NBP=10%, reaction temperature=100° C., and reaction time=1 hour (FIG. 5A). The color changes indicated that concentrations of MeBr from 10-100 ppm could be detected by comparing the color intensities (FIG. 5B).
Figure 5B:
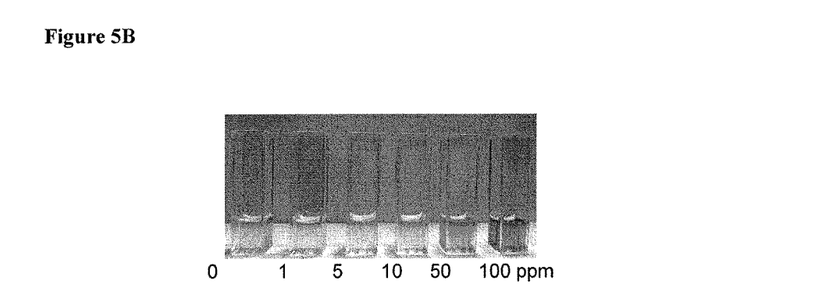
Figure 6:
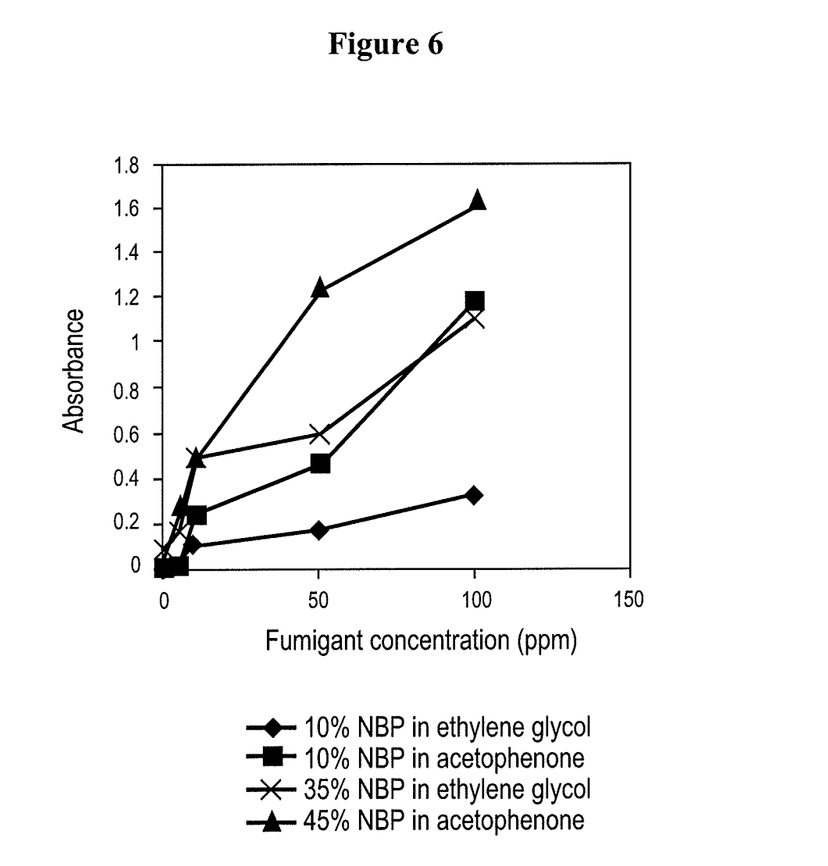
FIG. 6 shows the results from testing the sensitivity of NBP solutions to methyl iodide. NBP was dissolved in ethylene glycol or acetophenone, the solutions were exposed to methyl iodide, and a UV-Vis spectrometer was used to determine absorbance at the maximum absorbance wavelengths of each solvent. At concentrations of 10% and 45% NBP by weight of the solution, acetophenone solutions show higher absorbance.

NBP was dissolved in ethylene glycol or acetophenone, the solutions were exposed to methyl iodide, and a UV-Vis spectrometer was used to determine absorbance at the maximum absorbance wavelengths of each solvent. At concentrations of 10% and 45% NBP by weight of the solution, acetophenone solutions show higher absorbance. The results are shown in FIG. 6.

Example 7

Testing Solid Support and Loading of NBP Solutions

A solution of 80% NBP in acetophenone by weight of the solution was used for this experiment. A solution in the amount of 30 microliter, 40 microliter, 50 microliter, or 60 microliter was then spotted on cellulose grade 3 filter paper and microfiber (GF/F) grade filter paper. The spotted solid supports were exposed to 20 ppm methyl iodide for three minutes and the intensity of color developed on the solid support was compared. A microfiber (GF/F) grade filter paper provided deeper blue color spots.

A solution of 80% NBP in acetophenone by weight of the solution was used for this experiment. 30 microliter, 40 microliter, 50 microliter, 60 microliter and 70 microliter of the solution was then spotted on microfiber (GF/F) grade filter paper. The spotted solid supports were exposed to 20 ppm methyl iodide for three minutes and the intensity of color developed on the solid support was compared for each loading. The preferred amount of NBP to be added to the filter paper was found to be 60 microliter.

Solutions comprising 20%, 40%, 60% and 80% NBP in acetophenone by weight of the solution were prepared for this experiment. 30 microliter of each solution was spotted on cellulose grade 3 filter paper. The spotted solid supports were exposed to 20 ppm methyl iodide for three minutes and the intensity of color developed on the solid support was compared. The solution strength which provided deeper blue spots was 80% NBP in acetophenone by weight of the solution.

Example 8

Paper Based Sensor

Figure 7A:
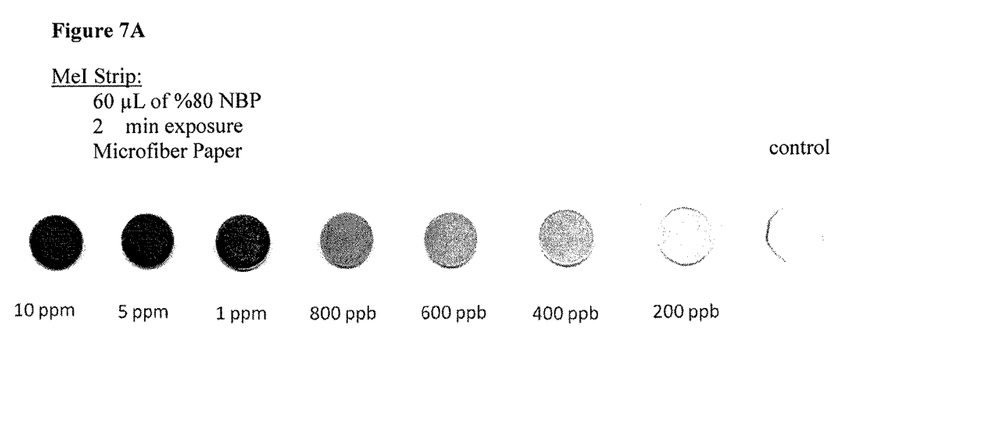
Figure 7B:
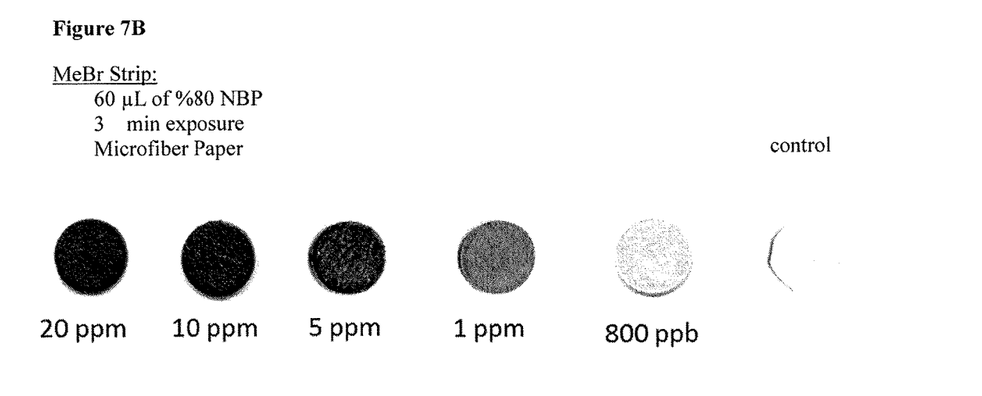

NBP was dissolved in acetophenone to reach 80% wt concentration. A filter paper strip was saturated with a certain amount of the solution. The paper based sensor was exposed to vaporous gases in a gas chamber for less than two minutes. A blue color appeared and was compared with a color chart quantifying the amount of the chemical in the vapor. FIG. 7 shows the results from this experiment. FIG. 7A shows results following exposure to methyl iodide, the far right is a control. FIG. 7B shows results following exposure to methyl bromide, the far right is a control.

All patents, patent applications, publications and presentations referred to herein are incorporated by reference in their entirety. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter.

What is claimed is:

1. A method for detecting an alkylating agent, the method comprising:

contacting the alkylating agent with a sensor moiety of the formula:

Formula I $(R)_{0-1}$ wherein R, when present, is selected from $(NO_2)_{1-2}$, $(NO_2)_{1-2}$, thiophenyl, $(NO_2)_{0-2}$, or a pi-conjugated oligomer, where the wavy line indicates the point of attachment to the rest of the molecule, without being under alkaline conditions; and detecting by the naked eye a change in light absorbance of the sensor moiety.

2. The method of claim 1, wherein the sensor moiety is selected from the group consisting of and

3. The method of claim 1, wherein the sensor moiety is 4-(p-nitrobenzyl)-pyridine (NBP) having the structure:

4. The method of claim 1, wherein the sensor moiety is 4-(thiophen-3-yl)pyridine having the structure:

5. The method of claim 1, wherein the alkylating agent is a fumigant.

6. The method of claim 5, wherein the fumigant is a field fumigant.

7. The method of claim 6, wherein the field fumigant is selected from the group consisting of methyl bromide, methyl iodide, 1,3 dichloropropene, formaldehyde, ethylene dibromide, and methyl isothiocyanate.

8. The method of claim 6, wherein the field fumigant is selected from the group consisting of methyl bromide, methyl iodide, 1,3 dichloropropene, formaldehyde and ethylene dibromide.

9. The method of claim 6, wherein the field fumigant is selected from the group consisting of methyl bromide, 1,3 dichloropropene, and methyl iodide.

10. The method of claim 1, wherein the detection is carried out visually by contacting a fumigant with a solution comprising the sensor moiety without the use of alkaline conditions and/or heat.

11. The method of claim 10, wherein the solvent for the solution comprising the sensor moiety is a ketone.

12. The method of claim 10, wherein the solvent for the solution comprising the sensor moiety is acetophenone.

13. The method of claim 1, wherein the detection is carried out visually by contacting a fumigant with a solution comprising the sensor moiety under alkaline conditions and detecting a color change under alkaline conditions.

14. The method of claim 1, wherein the detection is carried out visually by contacting a fumigant with a solution comprising the sensor moiety at an elevated temperature and detecting a color change at the elevated temperature, which is 20° C. to 100° C.

* * * * *